US006602422B1

(12) United States Patent
Miltenyi et al.

(10) Patent No.: US 6,602,422 B1

(45) Date of Patent: Aug. 5, 2003

(54) MICRO COLUMN SYSTEM

(75) Inventors: Stefan Miltenyi, Bergisch Gladbach (DE); Gregor Siebenkotten, Koln (DE); Mathias Koester, Koln (DE)

(73) Assignee: Miltenyi Biotech GmbH, Gladbach (DE)

( * ) Notice: Subject to any disclaimer, the term of this patent is extended or adjusted under 35 U.S.C. 154(b) by 0 days.

(21) Appl. No.: 09/456,128

(22) Filed: Dec. 7, 1999

Related U.S. Application Data

(62) Division of application No. 09/042,178, filed on Mar. 12, 1998, now abandoned.

(51) Int. Cl.[7] ........................ B01D 35/06; B03C 1/025; C12N 11/14; C12N 13/00

(52) U.S. Cl. .................... 210/695; 210/748; 435/173.1; 435/173.4; 435/173.9; 435/176

(58) Field of Search ................................ 210/222–223, 210/695, 724, 737, 749, 748, 766, 661, 663; 422/186.01, 82.12, 947, 7.1, 262; 435/270, 526, 525, 515, 173.1, 173.4, 173.9, 175–176

(56) References Cited

U.S. PATENT DOCUMENTS 3,970,518 A * 7/1976 Giaever ...................... 210/222
4,230,685 A * 10/1980 Senyei et al.
4,508,625 A 4/1985 Graham
4,664,796 A 5/1987 Graham et al.
4,666,595 A 5/1987 Graham
4,701,261 A * 10/1987 Gibbs et al. ................ 210/606
5,108,933 A * 4/1992 Liberti et al.
5,200,084 A * 4/1993 Liberti et al. ............... 210/695
5,336,760 A * 8/1994 Hardwick et al.
5,385,707 A * 1/1995 Miltenyi et al.
5,411,863 A * 5/1995 Miltenyi
5,439,586 A 8/1995 Richards et al.
5,543,289 A 8/1996 Miltenyi
5,646,001 A * 7/1997 Terstappen et al.
5,691,208 A 11/1997 Miltenyi et al.
5,693,539 A * 12/1997 Miltenyi et al.
5,705,059 A 1/1998 Miltenyi
5,711,871 A * 1/1998 Miltenyi ...................... 210/86
6,020,210 A * 2/2000 Miltenyi

FOREIGN PATENT DOCUMENTS

DE WO-93/03374 A * 2/1993
GB WO-92/16301 A * 10/1992
JP 53073672 A 6/1978
WO WO 92 16301 A 10/1992
WO WO-96/26782 A * 9/1996
WO WO96-26782 * 9/1996

OTHER PUBLICATIONS

Paul et al. (1981) "A bench top magnetic separator for malarial parasite concentration," *IEEE Transactions on Magnetics* MAG–17(6): 2822–2824.

* cited by examiner

*Primary Examiner*—Matthew O. Savage
*Assistant Examiner*—Marianne Ocampo
(74) *Attorney, Agent, or Firm*—Alan W. Cannon; Bozicevic, Field & Francis LLP

(57) ABSTRACT

A separation and release process for purifying biological material on a micro separation column includes release of the biological material from magnetic carriers and elution from the micro separation column while the magnetic carriers are still magnetically retained by a matrix of ferromagnetic particles inside the micro separation column.

14 Claims, 7 Drawing Sheets

200
222
216

200
222
216
222
α

200
210
212
220
214
216
218
212
214
216
212
214
216
218
214
216
212

MICRO COLUMN SYSTEM

This application is a divisional of U.S. application Ser. No. 09/042,178, filed Mar. 12, 1998, entitled "MAGNETIC MICRO SEPARATION COLUMN AND METHOD OF USING IT (AS AMENDED)", now abandoned. U.S. application Ser. No. 09/042,178 is hereby incorporated, by reference thereto. in its entirety.

TECHNICAL FIELD

The present invention relates to the application of high gradient magnetic separation (HGMS) to the separation of biological materials, including cells, organelles and other biological materials. Specifically, this invention relates to micro columns and micro column systems for high gradient magnetic field separation of macromolecules and cells.

BACKGROUND ART

High gradient magnetic separation (HGMS) refers to a process for selectively retaining magnetic materials in a chamber or column disposed in a magnetic field. This technique can also be applied to non-magnetic targets labeled with magnetic particles. This technique is thoroughly discussed in U.S. Pat. Nos. 5,411,863 and 5,385,707, which are hereby incorporated by reference in their entireties.

The material of interest, being either magnetic or coupled to a magnetic particle, is suspended in a fluid and applied to the chamber. In the presence of a magnetic field supplied across the chamber, the material of interest, being magnetic, is retained in the chamber. Materials which are non-magnetic and do not have magnetic labels pass through the chamber. The retained materials can then be eluted by changing the strength of, or by eliminating the magnetic field.

U.S. Pat. No. 4,508,625 to Graham (Graham '625), discloses a process of contacting chelated paramagnetic ions with particles having a negative surface charge and contained in a carrier liquid to increase the magnetic susceptibility of the particles. A magnetic field is then applied to the carrier liquid and particles to separate a t least a portion of the particles from the carrier liquid.

U.S. Pat. No. 4,666,595 to Graham (Graham '595), discloses an apparatus for dislodging intact biological cells from a fluid medium by HGMS. The fluid containing the cells is passed through a flow chamber containing a separation matrix having interstices through which the fluid passes. The matrix is subjected to a strong magnetic field during the time that the fluid passes therethrough. At least some of the cells are thereby magnetically retained by the matrix while the rest of the fluid passes therethrough.

Graham '595 further discloses a piezoelectric transducer in fluid communication with the matrix by means of the carrier fluid. When the matrix reaches its loading capacity for cells, the carrier fluid is replaced by an elutriation fluid. The piezoelectric transducer is then excited, to generate high frequency acoustic waves through the fluid in the chamber. The acoustic waves dislodge the cells (particles) from the matrix and are carried out by the elutriation fluid.

U.S. Pat. No. 4,664,796 to Graham et al. (Graham et al. '796) discloses an HGMS system for separating intact biological cells from a fluid medium. The system includes a flow chamber containing a separation matrix having interstices through which the fluid passes, and an associated magnetizing apparatus for coupling magnetic flux with the matrix. The magnetizing apparatus includes a permanent magnet having opposing North and South poles, and field guiding pole pieces. The flux coupler is positioned to pass a strong magnetic field through the matrix during the time that the carrier fluid passes therethrough to permit capture of the cells or particles by the matrix.

The flux coupler is positioned so that the magnetic flux is diverted away from the matrix during the elutriation phase, when the carrier fluid is replaced by an elutriation fluid, so that the viscous forces of the elutriation fluid exceed the weakened magnetic attractive forces between the matrix and the cells or particles, thereby permitting the elutriation fluid to carry away the cells or particles. Additionally, a piezoelectric transducer may be provided to be used in conjunction with the diversion of the magnetic flux by the flux coupler during the elutriation phase, to allow for a slower flow of elutriation fluid.

The matrix is positioned within the flow chamber so as to be subjected to the full magnetic flux of the magnet when the flow chamber is in a first position, during separation of the cells from the carrier fluid. When the flow chamber is rotated approximately 90° from the first position, during the elutriation phase, the matrix is positioned such that the magnetic flux substantially bypasses the matrix.

Graham et al. '795 further discloses the option of using a piezoelectric transducer in fluid communication with the matrix for use in conjunction with the positioning of the flux coupler to bypass the strong magnetic field around the matrix, to allow lower flow rates of the elutriation fluid.

The prior art addresses various methods of HGMS and methods of recapturing the cells/particles once they have been separated by HGMS. For very small samples, however, such as those encountered in molecular biology applications, the prior art is far from ideal for performing HGMS. Very small elution volumes are needed to efficiently elute very small samples, such as, for example, in the separation of messenger RNA from total RNA or cell lysates. Larger elution volumes require larger volumes of enzymes for downstream applications, which become prohibitively expensive and render the procedure inefficient and unusable. Additionally, small void volumes are important in situations where chemical reactions are intended to be performed within the column itself. The present invention is directed to more efficient and effective use of the HGMS technique for separation of very small samples, especially for use in clinical and commercial settings.

DISCLOSURE OF THE INVENTION

The present invention provides improvements in high gradient magnetic separation of materials contained within very small volumes. The present invention combines the advantages of a binding reaction in suspension (e.g., fast kinetics, high efficiency) with those of a separation on a column (e.g., purity, simplicity), while at the same time keeping the elution volume requirements low. Also, a small void volume is provided for performance of chemical reactions within the column.

The separation techniques may be employed in a continuous process or sequential processes, with the different steps of the separation being performed by simply adding different buffers, chemicals, etc., also with potentially different temperatures, e.g., hot water, etc., into a column. Thus, the complete procedure is very fast.

The present invention provides a micro separation column having first and second tubular portions, where the first portion is integral with the second portion. The first portion has a first cross sectional area which is unequal to the cross sectional area of the second portion. A matrix which is adapted to selectively remove at least one component of a mixture as the mixture flows through the tube is contained in at least part of the first portion and at least part of the second portion.

The matrix contains ferromagnetic material, preferably ferromagnetic balls or other ferromagnetic particles. The ferromagnetic material may be coated with a coating which maintains the relative position of the particles with respect to one another. Preferably, the coating comprises lacquer, and more preferably, a lacquer as described in at least one of U.S. Pat. Nos. 5,691,208; 5,693,539; 5,705,059; and 5,711,871, each of which are hereby incorporated by reference in their entireties. The ferromagnetic balls or particles preferably have a diameter or size of at least 100 μm, more preferably greater than about 200 μm and less than about 2000 μm, still more preferably greater than about 200 μm and less than about 1000 μm, and most preferably about 280 μm. The matrix (i.e., ferromagnetic particles and coating) preferably occupies at least about 50 percent of the internal volume of the first and second portions. The void volume of the column, that is the interstitial volume which is not occupied by the matrix (i.e., the matrix void volume) and the volume of the portion of the column that is below the matrix is preferably less than about 85 μl, more preferably less than about 70 μl, still more preferably less than about 50 μl, and most preferably about 30 μl. The self-adjusting, gravitational flow speed is generally greater than about 100 μl/min, more preferably greater than about 200 μl/min and most preferably greater than about 300 μl/min.

The tube may further comprise a third portion which is integral with the second portion. The third portion has a third cross sectional area which is less than the cross sectional area of the second portion. Still further, the tube may include a fourth portion integral with the third portion. The fourth portion has an outside dimension (e.g., and outside diameter, but may be an outside dimension of a structure which is other than circularly shaped in cross-section) which is less than a respective outside dimension of the third portion. An upper portion may be provided which is integral with the first portion. The upper portion has an cross sectional area which is greater than the cross sectional area of the first portion.

Optionally, the micro separation column may include a retainer located in the second portion adjacent the matrix. Preferably, the retainer is substantially spherical, and is substantially larger than the particles that make up the matrix. Alternatively, the retainer may be a porous mesh or grid or frit.

The tube may be formed from a material such as PCTG, polyethylenes, polyamids, polypropylenes, acrylics, PET, other plastics which are currently used for single use laboratory products, and glass, and is preferably formed of a plastic that will bind to lacquer, most preferably PCTG.

When a spherical retainer is employed, at least one mount preferably extends into the second portion of the tube for resting the retainer thereon. Preferably, three mounts are provided for support of the preferred spherically shaped retainer.

Optionally, an upper matrix retainer may be located in the first portion of the tube, adjacent the matrix. Preferably, the upper matrix retainer comprises a porous grid or mesh or frit. In addition to ferromagnetic materials, the matrix may optional include one or more nonmagnetic components, such as glass particles including spheres, or plastic particles or spheres.

Preferably, the micro separation column of the present invention is designed to operate by gravity feed, but may alternatively be designed to operate under a pressure feed.

A micro separation column according to the present invention includes first and second tubular portions, with the first portion being integral with the second portion, and a matrix adapted to selectively remove at least one component of a mixture as the mixture flows through the tubular portions. The matrix is contained in at least part of the first portion and at least part of the second portion. The portion of the matrix which is contained in the first portion accomplishes a greater removal function than the amount of matrix that is contained in the second portion. The amount of matrix in the second portion accomplishes a greater flow resistance function than the amount of matrix contained in the first portion. Preferably, the overall height of the matrix is less than about 20 mm, more preferably less than about 15 mm, and most preferably less than about 12 mm. Preferably, the height of the matrix in the first portion is less than about 10 mm, more preferably less than about 6 mm.

Further disclosed is a micro separation unit for use in performing micro separation. The micro separation unit includes a magnetic yoke having at least one notch formed along a length thereof. A pair of magnets is placed within each notch. Each pair of magnets defines a gap therebetween, which is adapted to receive a micro separation column therein for performance of micro separation. Preferably, the yoke is made of steel. Preferably, the yoke includes at least two notches and more preferably, four.

Each pair of magnets forms a magnetic field in each respective gap of greater than about 0.2 Tesla, preferably greater than about 0.4 Tesla, more preferably greater than about 0.5 Tesla, and most preferably greater than about 0.6 Tesla.

The micro separation unit further includes a non-fragile covering encasing the yoke and the magnets. Preferably, the covering is made of polyurethane rubber. At least one mounting magnet may be further provided within the covering for magnetically mounting the micro separation unit to a magnetic surface.

A micro column system according to the present invention includes a micro separation unit comprising a magnetic yoke having at least one notch formed along a length thereof, and a pair of magnets placed within each of said at least one notch to form a gap therebetween; and at least one micro separation column, each comprising: first and second tubular portions, with the first portion being integral with the second portion, and a matrix adapted to selectively remove at least one component of a mixture as the mixture flows through the tubular portions. The matrix is contained in at least part of the first portion and at least part of the second portion. The part of the matrix contained in the first portion accomplishes a greater removal function than the amount of matrix contained in the second portion. The number of micro separation columns equals the number of said gaps contained in the yoke.

Another aspect of the present invention is related to a separation and release process for purifying biological material on the micro column. After retaining the biological material of interest coupled to magnetic particles in the matrix, the bound material may optionally be dissociated from the magnetic particles and eluted from the column while the magnetic particles are still magnetically retained by the matrix. The dissociation may be performed by an adequate change of buffers, temperature, chemical or enzymatic reaction which dissociates the link between the magnetic particles and the biological material of interest.

BEST MODE FOR CARRYING OUT THE INVENTION

Figure 1:
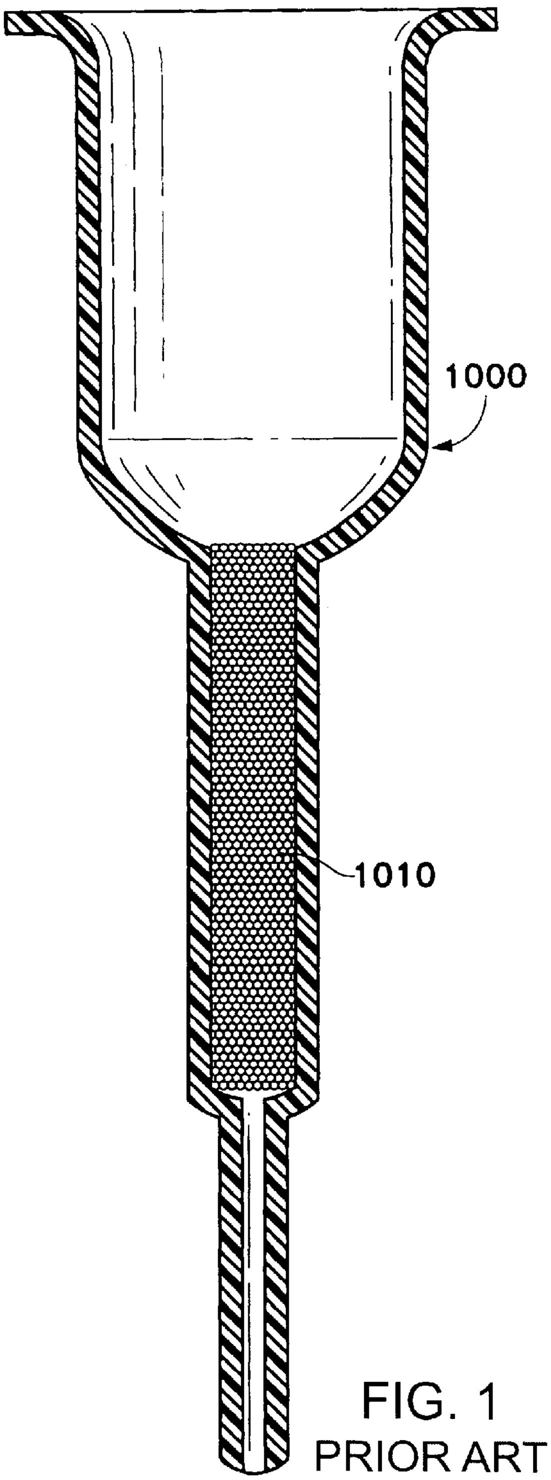
FIG. 1 PRIOR ART
FIG. 1 is a sectional view of a prior art column.

The separation of very small samples such as those encountered in many molecular biology applications, e.g., MRNA, by HGMS calls for the use of very small elution volumes to efficiently and effectively elute the samples, and for reaction in a small volume, a small void volume is also required. As an illustration of the need, a prior art column such as that shown in FIG. 1 includes a matrix 1010 of metal spheres of about 280 μm size which give a porosity of about 28 μm. The column height of the matrix 1010 is about 20 mm, the void volume of the matrix 1010 is about 70 μl, and the void volume of the column is about 85 μl. The flow rate through the matrix of spheres is about 400 μl/min.

A simple reduction in the column height of the matrix 1010, while serving to reduce the volume of the same, is not effective in processing the small samples referred to since the resultant flow rate through the matrix is too great. A reduction in the cross sectional area of the matrix increases the probability of clogging as well as reducing separation speed. A reduction in the height of the fluid column reduces and possibly eliminates drip formation at the end of the column, since the pressure head generated must be great enough to overcome the surface tension at the end of the column where the drips form.

Figure 2:
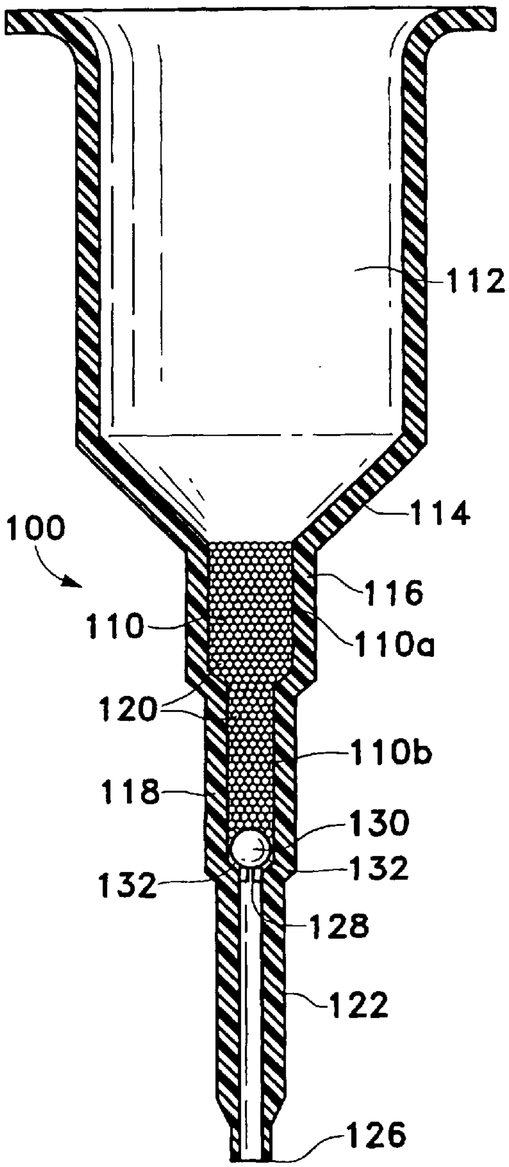
FIG. 2 is a sectional view of a preferred embodiment of a micro column according to the present invention.

The present invention successfully addresses all of the above-mentioned potential problems. A preferred embodiment of the present invention 100 is shown in FIG. 2. The micro column 100 is substantially reduced in void volume in comparison to columns used in the prior art, while maintaining optimal flow speeds, and is designed for the separation of macromolecules (or cells), that are magnetically bound via specific biological/chemical interactions, from other molecules (or cells) in a high gradient magnetic field and for the elution of these molecules/cells in a small volume. The micro column is made hydrophilic by manufacturing it from a hydrophilic material such as a hydrophilic plastic, or, more preferably, by coating the column interiorly with a hydrophilic material, e.g., polyvinyl pyrrolidone. Alternatively, or in addition thereto, buffers which are poured into the column may contain one or more surfactants, e.g., SDS.

The matrix 110 includes a first portion 110*a* having a relatively larger cross sectional area than that of a second portion 110*b*. The column 100 includes a relatively large volume reservoir 112 into which a sample to be separated is poured. The reservoir 112 funnels 114 into a smaller cross sectional area first portion 116 of the column that houses the first portion 110*a* of the matrix. The first portion narrows down to an even smaller cross sectional area second portion 118 of the column that houses the second portion 110*b* of the matrix. Although all of the columns shown in the Figures are of the preferred cylindrical configuration, the present invention is not to be so limited. For example, the columns may be formed to have an elliptical cross-section, a square cross section, other geometric cross-sections or even non-geometric cross-sections. Additionally, the shapes of the portions do not have to be alike. For example, a first portion might have a hexagonal cross-section while the second portion might be cylindrical.

The matrix 110 contains ferromagnetic material, preferably balls 120, but may be other particles which are not spherical, or an integrated three dimensional mesh having the desired porosity. The ferromagnetic material 120 may be coated with a coating which maintains the relative position of the particles with respect to one another. Preferably, the coating is a lacquer. The balls/particles have a size greater than about 100 μm, preferably greater than about 200 μm and less than about 2000 μm, more preferably greater than about 200 μm and less than about 1000 μm, and most preferably about 280 μm. Examples of separation matrices which are useful for HGMS are more thoroughly described in copending application No. 08/377,744, filed Jan. 23, 1995, as well as U.S. Pat. No. 5,411,863, both of which are hereby incorporated by reference thereto in their entireties. The matrix preferably occupies at least 50 percent of the internal volume of the first and second portions.

The column 100 is preferably made of plastics such as polypropylenes, polyethylenes, acrylics, PET, etc, and, when the matrix is coated with lacquer, is preferably made of a plastic that will bind with lacquer, most preferably a resin such as PCTG (polycyclohexadimethylterephtalate modified with Ethylenglycol). This makes the production of the columns much simpler, since it eliminates a need to remove excess lacquer after the step of pouring lacquer into the column to coat the ferromagnetic particles. When the column is made of a material such as polypropylene, the excess lacquer must be removed from the walls of the column after coating the ferromagnetic particles. This is a time consuming, tedious step which significantly increases the cost of production of the columns.

A high gradient magnetic field is generated in the matrix 110 upon insertion into an external magnetic field. The matrix readily demagnetizes when it is taken out of the field. The flow rate is lower in the first portion 110*a* of the matrix than in the second portion 110*b*. The first portion 110*a* of the matrix primarily performs the separation function, since it is of a larger cross sectional area and volume that the second portion 110*b*. The magnetized particles of the matrix 110 retain single superparamagnetic MicroBeads (of an average diameter of 50 nm/as specified by Miltenyi Biotec) and material attached to them from a solution or reaction mixture of variable viscosity, which flows through the column 100, preferably by gravity. The bound material can be eluted in a small volume. The second portion **110*b* primarily performs a flow resistor function, since it is of a significantly lesser cross-sectional area than the first portion 110*a* and also may be formed of smaller size particles. Of course, the first portion 110*a* also performs as a resistive element to some extent. The second portion 110*b*** preferably functions as a separator somewhat, although it may alternatively be formed entirely of nonmagnetic particles such as plastic or glass, in which case, it would function only as a resistive element.

Figure 5:
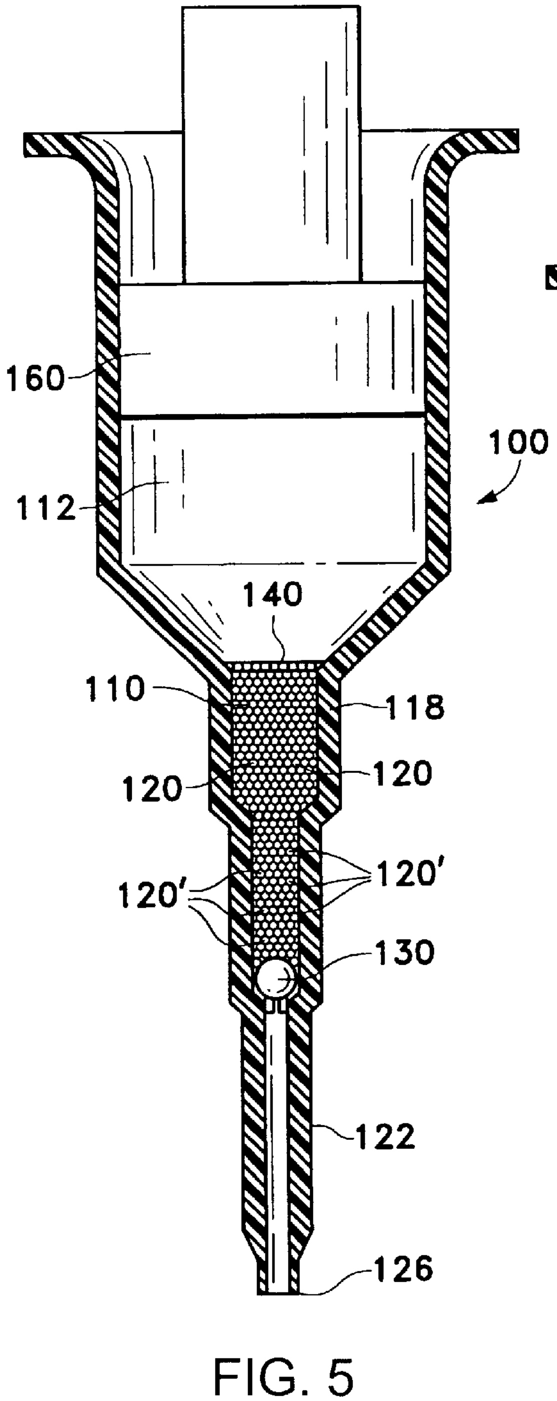
FIG. 5 is a sectional view of a variation of the micro column according to the present invention.

Thus, glass balls/particles 120' or plastic balls/particles or other non-ferromagnetic balls or particles may be substituted for some of balls/particles 120 in the first and/or second portions without unduly affecting the separation capability of the column and matrix, and without affecting the resistive function of the second portion, see FIG. 5. In some instances, all of the balls/particles 120 in the second portion may be so substituted. Preferably, the micro separation column of the present invention is designed to operate by gravity feed, but may alternatively be designed to operate under a pressure feed. To permit this, a plunger 160 fits into the reservoir 112 and can be used to flush out the bound material. In addition, bound material (e.g., cells) can be eluted in a minimum volume by centrifugation.

A porous frit or grid 140 may be positioned adjacent the top end of the matrix 110, particularly for those embodiments having particles or balls which are freely displaceable, i.e., not held in place by a lacquer or other binding agent. The porous frit/grid is preferably made of glass or plastic or metal mesh and has a pore size greater than or equal to the pore size of the matrix and less than the particle/ball size of the matrix.

Figure 6:
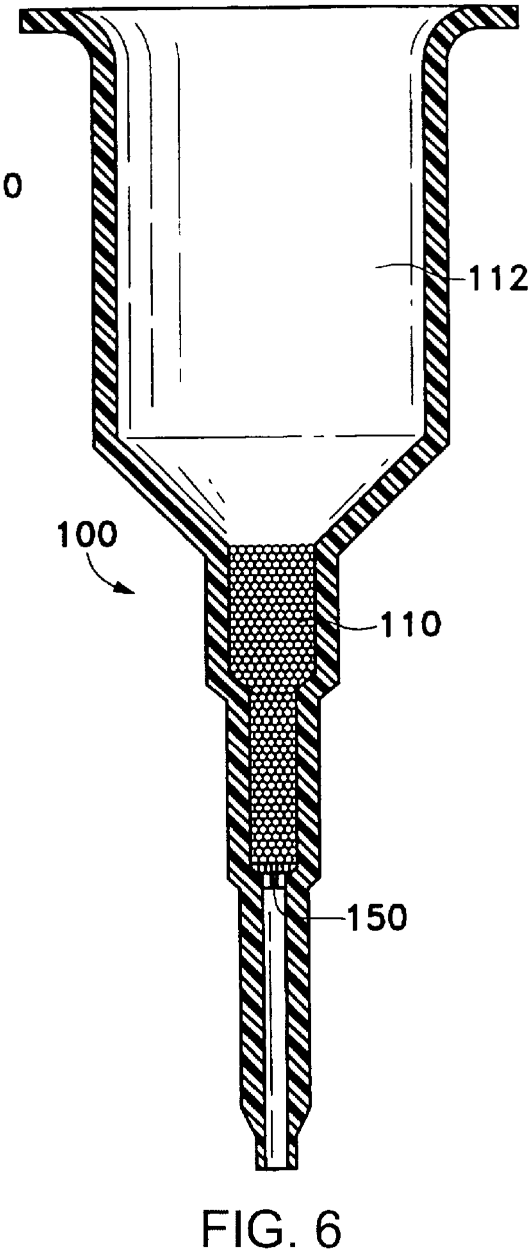
FIG. 6 is a sectional view showing another variation in the micro column according to the present invention.

In place of the ball shaped retainer 130, a porous frit or grid 150 may be positioned adjacent the bottom end of the matrix 110, for those embodiments having particles or balls which are freely displaceable, as well as for those held in place by a lacquer or other binding agent, see FIG. 6. The porous frit or grid is preferably made of glass or plastic or metal mesh and has a pore size greater than or equal to the pore size of the matrix and less than the particle/ball size of the matrix.

When balls 120 are used to form the matrix 110, the ball size is greater than 100 μm, preferably greater than about 200 μm and less than about 2000 μm, more preferably greater than about 200 μm and less than about 1000 μm, and most preferably approximately 280 μm. Of course, the size of the balls may be modified to calibrate or vary a desired rate of flow through the matrix. However, too great a reduction in the ball size can lead to clogging because of the concurrent reduction in the pore size in between the balls. On the other hand, too great an increase in the size of the balls can lead to a flow rate which is unacceptably fast, which negatively effects the per cent retention of the magnetic particles.

A minimum height of the fluid column (i.e., the height of the fluid above the tip end of the column) is required to generate sufficient pressure to overcome the surface tension where drop formation occurs, to ensure a proper flow. The second portion **110*b* effectively increases the resistance and allows a lower overall height of matrix 110 to be used, thereby also reducing the effective volume of the matrix 110. The overall height of the matrix 110** is less than about 20 mm and preferably is less than about 15 mm, most preferably less than about 12 mm. Where small elution volumes are important, the void volume of the column, i.e. the interstitial area within the matrix that is not occupied by the balls/particles and the volume of the column extending beneath the matrix, is generally less than about 85 μl, preferably less than about 70 μl, more preferably less than about 50 μl, and most preferably about 30 μl.

Another factor to be considered in designing a column is the surface tension that is generated at the end of the column where drops form as the liquid exits the column. As the column length or height increases, a greater pressure head is developed to overcome the surface tension. If the surface tension is too great relative to the pressure head, drop formation at the end of the column will be compromised and possibly even prevented, thereby halting flow through the column. Thus, it is necessary to form a third portion 122 of the column, to extend the length to the end 126. The third portion 122 has a smaller inside cross sectional area than the second portion 118, as well as a smaller outside dimension (e.g., diameter, in the case of a cylindrical portion). The length of the third portion may vary according to the respective cross sectional areas and the desired flow rate.

Table 1 shows the effect of first, second and third portion cross sectional areas and heights on flow rate and the correlation between flow rate and percentage recovery of MicroBeads.

TABLE 1

Recovery in correlation to the flow rate.

| Matrix diameter x height mm | 2nd Matrix diameter x height mm | Extension diameter x height mm | Flow rate ml/min | Recovered MicroBeads % |
|---|---|---|---|---|
| 3 × 5 | 1.9 × 2.7 | 0.8 × 12 | 0.64 | 69 |
| 3 × 5 | 1.9 × 3.5 | 0.8 × 12 | 0.45 | 76 |
| 3 × 5 | 1.9 × 4.5 | 0.8 × 12 | 0.40 | 81 |
| 3 × 5 | 1.9 × 6.0 | 0.8 × 12 | 0.26 | 94 |

Figure 3:
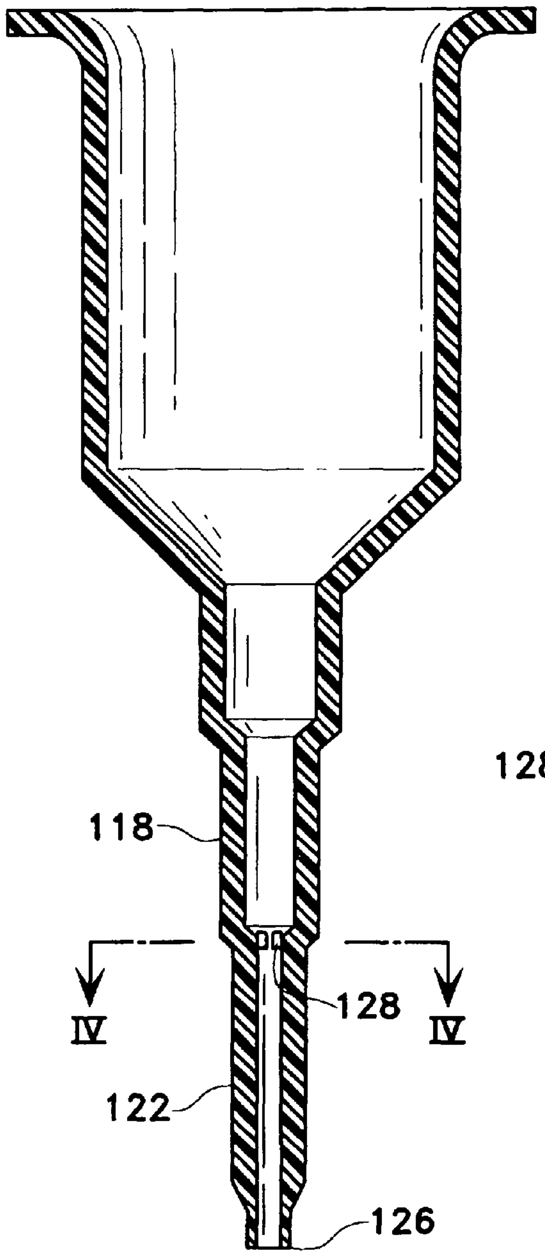
FIG. 3 is a sectional view of a micro column according to the present invention.
Figure 4:
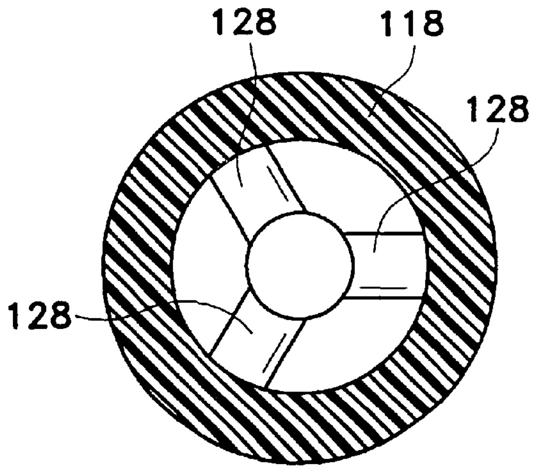
FIG. 4 is a sectional view of a column, the section being taken perpendicular to the section shown in FIG. 3 at a level indicated by lines IV—IV.

When using a spherical retainer 130, at least one mount 128 extends from the top end of the third portion 122 and into the second portion. Each mount 128 is preferably peg-shaped (see also FIG. 3). Preferably a set of three mounting elements 128 (see FIG. 4) extend from the third portion into the second portion and function to support the spherical retainer 130. Retainer 130 is preferably a ball that is substantially larger than the balls 120 and is sized to prevent the escape of balls 120 into the third portion during filling of the column 100 with the matrix 110 and all the time when the balls are not held in place with a lacquer. However, the retainer wall 130 also maintains passages which are at least as large as the spaces between balls 120 in the matrix 110 so as not to impede the flow of fluid though the second portion 118 and into the third portion 122.

The distal end of the third section 122 tapers into a tip 126. The outside dimension (e.g., outside diameter when the tip is the tip of a cylindrical tube) of the tip 126 is smaller than that of the third section and defines the preferred drop size of fluid to exit the column. One preferred embodiment has an outside diameter of about 1.5 mm, but of course, this dimension may be varied by shaping the end or "nozzle" of the column according to the drop size that is desired.

Another aspect of the invention is related to a separation and release process for purifying biological material on the column 100. After retaining the biological material of interest coupled to magnetic particles in the matrix 110, the bound material may optionally be dissociated from the magnetic particles and eluted from the column 100 while the magnetic particles are still magnetically retained by the matrix 110. The dissociation may be performed by an adequate change of buffers, temperature, chemical or enzymatic reaction which dissociates the link between the magnetic particles and the biological material of interest. For example, mRNA may be released from Poly-T conjugated beads by a change of buffer composition and temperature preferentially above 30° C. Materials bound by antibodies, protein A or G may be released in the column by changing pH, salt conditions, chemicals (DTT for SPDP links) or introducing detergents, e.g., SDS or chaotropic agents.

Figure 7:
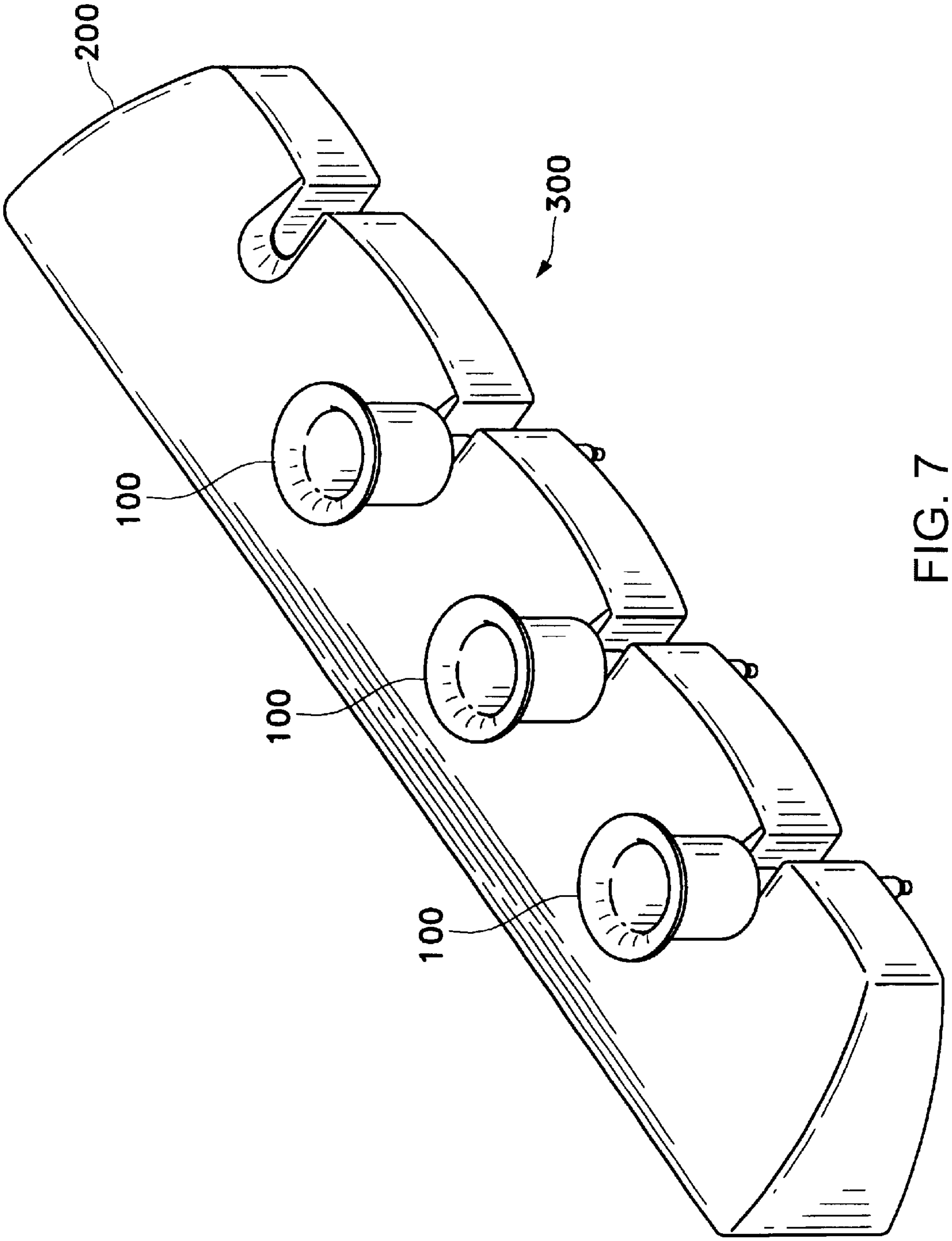
FIG. 7 is a perspective view of the micro column separation system according to the present invention.

The micro column 100 is designed for use in a micro column HGMS system according to the present invention. The system 300 includes a separation unit 200 which holds one or more micro columns 100 (four in the preferred embodiment) as shown in FIG. 7. The micro separation unit includes a yoke 210 that forms the basic framework of the unit and that concentrates the magnetic fields. The yoke is configured to include a notch 212 in the each area where processing with a micro column is intended to occur.

A pair of magnets 214 are mounted in each notch 212 so as to form a narrower gap 216 where the magnetic field of the magnets is focused and where a micro column is to be received for performing HGMS separation. As noted, in the preferred embodiment shown in the figures, the yoke 210 connects four pairs of strong permanent magnets (FIG. 8C), that cooperatively produce the magnetic field needed for four parallel separation processes in four columns. It is reiterated that, of course, the present invention is in no way to be limited to the configuration of four micro column stations, as other numbers could just as easily be configured.

Two magnets 218 are preferably connected to the back of the yoke 210 to facilitate attachment or mounting of the unit to a ferromagnetic device such as an iron stand. Again, a different number of magnets 218 might be used for mounting. Additionally, other mounting means such as clamps, screws, bolts, etc. could be alternatively or additionally employed.

The unit thus far described is entirely encased in a non-fragile covering 220. The non-fragile covering protects the internal components of the unit 200 as well as makes the unit more "user friendly" in that it is more pleasant to the touch (warmer, softer) and is much more easy to clean/sterilize. Preferably, the covering 220 is a layer of foam of a resin such as a polyurethane rubber, which protects the unit 200 against corrosion and chemical or mechanical damage. Other alternative covering materials that serve the same purpose may be employed.

Each gap 216 of the separation unit 200 has a magnetic field that is greater than 0.2 Tesla, preferably greater than 0.4 Tesla, more preferably greater than about 0.5 Tesla, and most preferably greater than about 0.6 Tesla. A preferred embodiment generates magnetic fields in the range of about 0.6–0.7 T. Table 2 shows the relationship between the strength of the applied magnetic field and the amount of MicroBeads that are recovered as a result thereof. The trend is the same, independent of the type of column used.

TABLE 2

Recovery of MicroBeads in correlation to the strength of the magnetic field.

| Magnetic field (Tesla) | Column I | Column II | Column III | Column IV | Column V |
|---|---|---|---|---|---|
| 0.5 | 74% | 75% | 64% | 52% | 81% |
| 0.6 | | 84% | 74% | | |
| 0.75 | 85% | 88% | 77% | 69% | 94% |

Figures 8A, 8B, 8C:
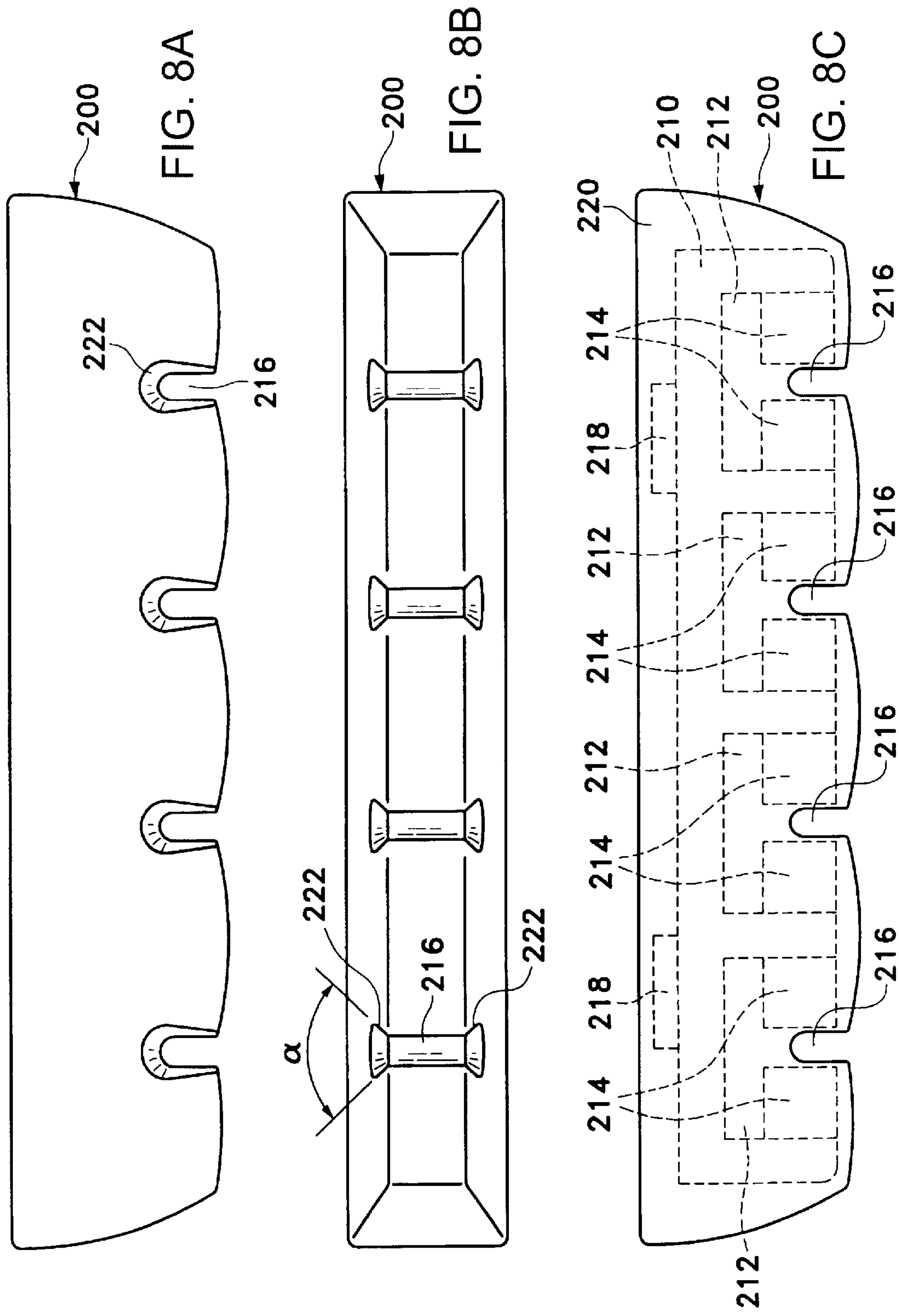
FIG. 8A is a top view of a separation unit according to the present invention.
FIG. 8B is a front view of the separation unit shown in FIG. 8A.
FIG. 8C is a top view of the separation unit, with the internal components shown in phantom lines.

As shown in FIGS. 8A and 8B, covering 220 forms bevels 222 at the top and bottom of each of the gaps 216. The bevels are designed to mate with the funneling portion 114 of the micro column, which further stabilizes the micro column in a vertical position within gap 216. The bevels 222 are formed at the top and bottom of each gap 216 to render the unit 200 symmetrical about its horizontal axis. Thus, the top and bottom of the unit are identical and it is therefore impossible for a user to employ the unit "upside down". As shown in FIG. 8B, the angle of the bevel 222 is preferably about 90°, but this angle can of course vary according to the slope of the funneling of a micro column to be held in the gap and bevel.

EXAMPLES

Example 1

To achieve a small elution volume (<50 μl) the part of the micro column filled with matrix had a total volume of 52 $mm^3$ leaving space for 22 μl of fluid (matrix volume) when standard ferromagnetic material was used (iron balls of an average diameter of 280 μm). Together with the volume in the portion 122 of the column, the void volume of the column that was relevant for the elution was 29 μl.

To ensure that more than 90% of the MicroBeads applied to the column (in a buffer containing detergent), (in a magnetic field of 0.6–0.7 T) were retained at a matrix of a height of 11 mm, the flow rate of the MicroBead suspension had to be regulated. For this reason the matrix was bipartite. The lower 6 mm part of the matrix (i.e., 110*b*) had an inside diameter of only 1.9 μm which had severe impact on the flow rate whereas the upper 5 mm of the matrix (i.e., 110*a*) had a larger diameter of 3 mm to decrease the probability of clogging of the column.

The matrix was delimited at the bottom by a steel ball (i.e., 130) of 1.6 mm diameter. Below this the inner cross sectional area of the tube (i.e., 122) was reduced to 0.8 mm. The steel ball was positioned on three bridges (i.e., mounts 128) that kept it from closing the tube. The steel ball prevented the ferromagnetic material from slipping out during the filling process.

To make sure that the column allowed drop formation by gravity when the buffer was applied on top of the matrix, the total height of the part of the column filled with buffer was empirically determined to be 24 mm. For that reason the column was extended beyond the matrix area by a tube 122 with a length of 12 mm and a diameter of 0.8 mm.

The matrix plus bottom extension had a calculated void volume of 29 μl. To achieve a minimal elution volume the first fraction of buffer that flowed from the column during such an elution (an amount of buffer that comes close to the void volume) could be skipped since it would not contain any of the eluted material. The buffer drop size is designed to be smaller than about 80% of the void volume of the column so that the first drop can be thrown out. For this reason the drop size of (detergent-free) buffer was defined to be approximately 24 μl. This was achieved by adjusting the diameter of the bottom tip of the column to 1.5 mm.

Figure 9:
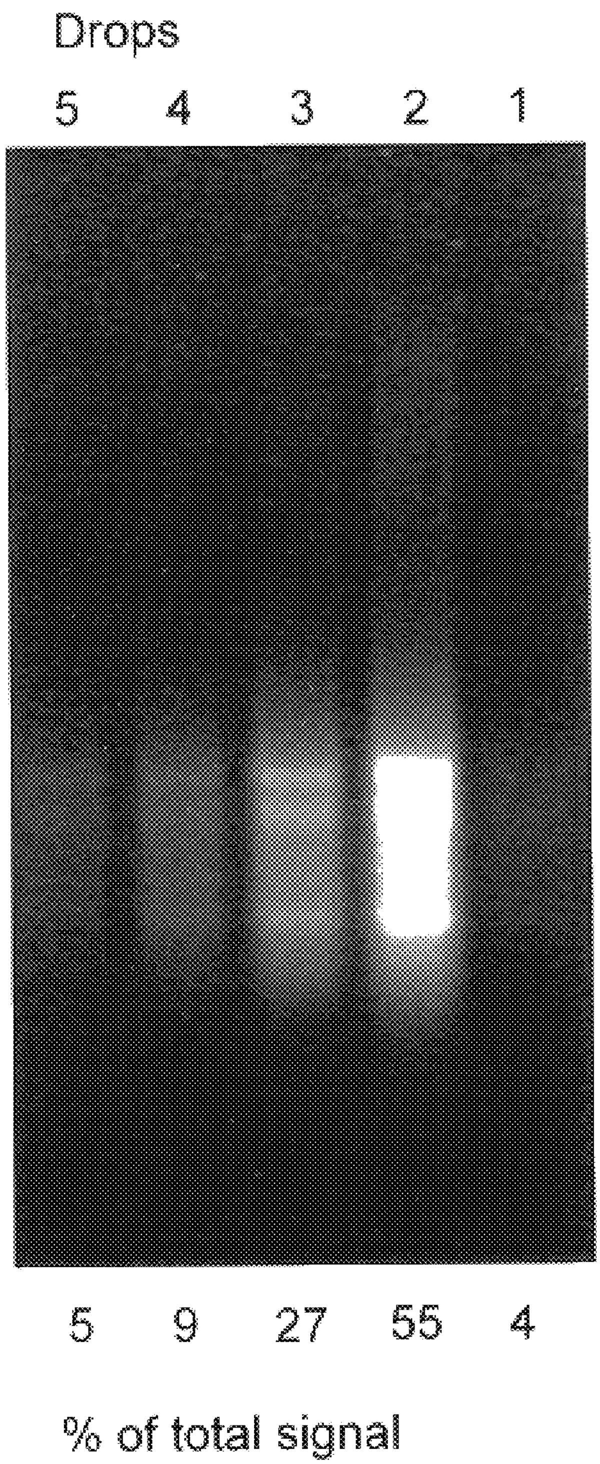
FIG. 9 shows the composition of drops 1 through 5 (percentage of the mRNA sample eluted) from Olig(dT) MicroBeads retained in a micro column system, as displayed on an agarose gel.

In addition, the controlled drop size led to a defined elution volume. Drops 2 and 3 contained >80% of the eluted material (see FIG. 9) and drops 2–4 contained >90% of the eluted material.

The micro columns 100 placed in the separation unit 200 described above can bind at least 2 mg of MicroBeads as determined by optical density of the MicroBeads at a wavelength of 450 nm (Table 1). About 90 to 98% of 0.1–2 mg basic MicroBeads (Miltenyi Biotec GmBH) applied to the column are retained in the magnetic field as determined by optical density of the MicroBeads at a wavelength of 450 nm (Table 1).

Since the flow rate is primarily maintained by the 1.9 mm diameter part of the matrix it is easy to reduce or enhance the flow rate by changing the diameter of the balls. The flow rate of buffer (containing detergent, 1% SDS) in a column with a standard matrix (280 μm balls) is 300 μl/min. The flow rate of a column with balls of an average diameter of 230 μm is 200 μl/min. The average flow rate of automatically produced columns with a matrix of 280 μm balls is 320+/−100 μl. The average drop size of water is 23.9 μl.

For many applications it is advantageous to elute the bound material from the MicroBeads while the MicroBeads are still bound to the matrix in the magnetic field. In this case the material is eluted by adding a different buffer that breaks the chemical interactions between the retained molecule and the catching agent. One example for the separation of macromolecules is the isolation of mRNA from crude cell extract via the specific interaction of oligo(dT) coupled to MicroBeads with the poly A tail of the mRNA. (Approximately 0.01% of the total cell mass is mRNA). $1\times10^7$ cultured hybridoma cells were washed in PBS, the pellet was resuspended and lysed in 1 ml of a lysis/binding buffer (0.1 M Tris/HCL pH 8.1, 1% SDS, 0.2M LiCl, 10 mM EDTA, 5 mM DDT. The SDS completely inactivates the activity of cellular RNAases, which are set free by the lysis.)

To strongly reduce the high viscosity of the lysate, caused by genomic DNA, it was centrifuged through a porous matrix (2 min. at 13000×g through three layers of blotting paper placed on a porous polypropylene filter. This procedure does not interfere with the integrity of the mRNA.)

50 μl of oligo(dT) MicroBeads were added to the lysate and the lysate was mixed. (For the hybridization of MRNA to oligo(dT) MicroBeads no additional incubation is necessary).

A column placed in the magnet was prepared by adding 100 μl of lysis/binding buffer. The lysate was added. After it had flowed through the matrix, two 250 μl aliquots of lysis/binding buffer were added, to wash away all unbound material (proteins, DNA) and four 250 μl aliquots of wash buffer (50 mM Tris/HCL pH 7.5, 25 mM NaCl, 1 mM EDTA) were added, to wash away all unspecifically bound material (rRNA, DNA).

To elute the mRNA from the MicroBeads, 200 μl of 65° C. elution buffer (1 mM EDTA) was added. Drops 1 through 5 were collected in separate tubes and analyzed on a 0.8% agarose gel stained with Ethidiumbromide (see FIG. 9).

TABLE 3

Percent recovery of approx. 100 μg of MicroBeads of different batches applied to different columns.

a) diameter of matrix balls: 230 μm

| | Batch A | Batch B | Batch C | Mean |
|---|---|---|---|---|
| Column 1 | 97 | 98.6 | 98.4 | 98 |
| Column 2 | 97.3 | 98.8 | 98.6 | 98.2 |
| Column 3 | 97 | 98.6 | 97.9 | 97.8 |
| Column 4 | 96 | 97.1 | 98 | 97 |
| | | | | 97.8 |

b) diameter of matrix balls: 280 μm

| | Batch A | Batch B | Batch C | Batch D | Batch B | Mean |
|---|---|---|---|---|---|---|
| Column 1 | 90.4 | 94.2 | 94 | 92.6 | 92.5 | 92.7 |
| Column 2 | 91.2 | 93.5 | 94 | 92.7 | 93.3 | 92.9 |
| Column 3 | 91.1 | 93.7 | 94.6 | 93.3 | 93.5 | 93.2 |
| Column 4 | 91.4 | 94.3 | 95.4 | 93.5 | 94 | 93.7 |
| | | | | | | 93.1 |

Percent recovery of approx. 2 mg. of MicroBeads of batch B applied to column 1.

Batch B

Column 1 97.8

Example 2

Immunomagnetic Isolation of Protein with Protein G MicroBeads

Another example for the separation of macromolecules is the isolation of protein from crude cell extract via antibodies, that bind to the protein and are then caught by protein G coupled to magnetic MicroBeads.

$1\times10^7$ mouse liver cells were lysed in 1 ml of a lysis buffer, that left the nuclei intact (150 mM NaCl, 1% Triton× 100, 50 mM Tris pH 8.1). The nuclei were removed by centrifugation. The supernatant was spiked with 100 ng of Phycoerythrin. It was then mixed with 1 μg of a monoclonal anti Phycoerythrin antibody and incubated at 6° C. for 5–30 min. 10 μl of Protein G MicroBeads (carrying 0.5 μg recombinant Protein G) were added, the reaction mixture was briefly mixed and incubated for an additional 5–30 min. at 6° C.

A Micro-column was placed in the described magnetic separator and prepared by washing with 100 μl of lysis buffer. The reaction mixture was applied onto the column. After the reaction mixture had completely flowed through the column, the column was washed by adding 3–125 μl lysis buffer and 4×with 125 μl PBS.

For elution the column was left in the magnetic separator and the buffer was exchanged by adding 50 μl of an SDS gel sample buffer (containing 1% SDS). The buffer was incubated in the column for 3 min. to dissolve the immunomagnetic complexes. Then the elution proceeded by adding 75 μl of sample buffer and collecting the drops (2–4), which contained the antigen and the antibody eluted from the column. Due to the surfactant (SDS) the drops have an average volume of 15 μl, thus the total elution volume is 45 μl.

Figure 10:
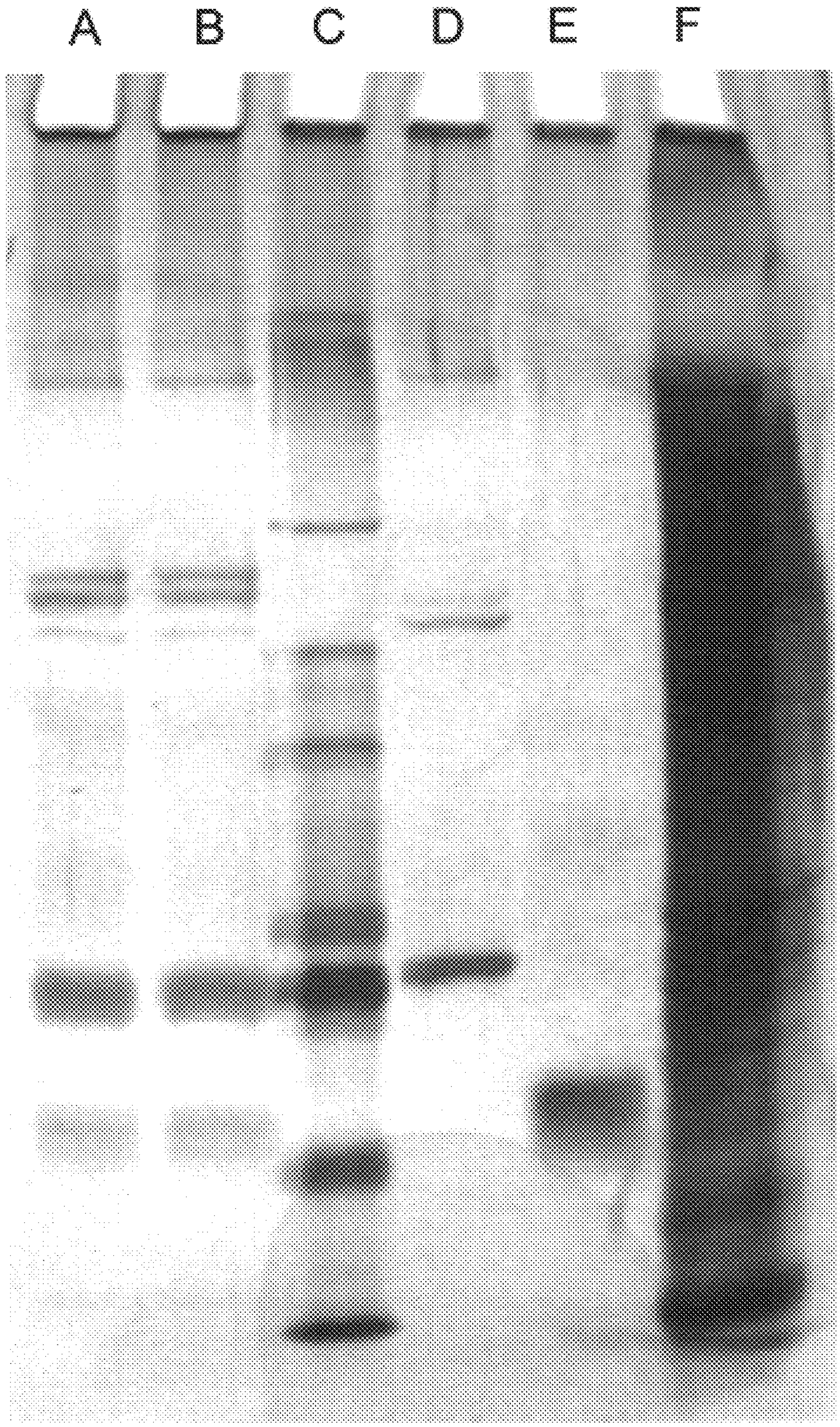
FIG. 10 shows the results of a separation analyzed on an SDS Polyacrylamide gel.

The separation was analyzed on an SDS Polyacrylamide gel, the results of which are shown in FIG. 10. Proteins were made visible by silver staining. "A" and "B" in FIG. 10 represent eluants of two independent isolations. "C" represents a size marker. "D" represents the anti Phycoerythrin antibody and "E" represents the Phycoerythrin. "F" represents the flow through of one separation.

This method of immunoaffinity purification can be performed in less than an hour. It omits the centrifugation steps and long incubation periods, typical for standard immunoprecipitation protocols. In addition it yields very high purities. With the highly sensitive silver staining procedure nearly only the antibody and the antigen is detectable on the SDS-PAGE shown.

What is claimed is:

1. A process for purifying biological material on a column, comprising:

retaining magnetic carriers bound to the biological material with ferromagnetic particles in a magnetic field in first and second tubular portions of a micro separation column, wherein said first and second tubular portions have different cross-sectional areas, each cross-sectional area having a substantially constant diameter; and eluting the biological material by dissociating the biological material from the magnetic carriers while still in a magnetic field.

2. The process of claim 1, wherein said eluting comprises a change of buffers.

3. The process of claim 1, wherein said eluting comprises a change of temperature.

4. The process of claim 1, wherein said eluting comprises a change of chemical or enzymatic reaction.

5. The process of claim 1, wherein the biological material comprises material bound by antibodies, protein A or protein G and wherein said eluting comprises changing pH, salt conditions, chemicals or introducing detergents.

6. The process of claim 1, wherein the biological material comprises mRNA, and wherein said eluting comprises a change of buffers and heating to a temperature above about 30° C.

7. The process of claim 1, wherein the matrix is contained in at least part of the first tubular portion and at least part of the second tubular portion.

8. A process for purifying biological material on a column, comprising:

providing a separation column containing a matrix including ferromagnetic material therein wherein said separation column includes first and second tubular portions, said first and second tubular portions have different cross-sectional areas, each cross-sectional area having a substantially constant diameter;

generating a high gradient magnetic field in the matrix;

flowing a fluid containing magnetic carriers bound to the biological material through the separation column, whereby the magnetic carriers are retained by the ferromagnetic material; and eluting the biological material by dissociating the biological material from the magnetic carriers while still in said magnetic field.

9. The process of claim 8, wherein the matrix is contained in at least part of the first tubular portion and at least part of the second tubular portion.

10. The process of claim 8, wherein said eluting comprises a change of buffers.

11. The process of claim 8, wherein said eluting comprises a change of temperature.

12. The process of claim 8, wherein said eluting comprises a change of chemical or enzymatic reaction.

13. A process for purifying biological material on a column, said process comprising the steps of:

retaining superparamagnetic carriers bound to the biological material with ferromagnetic particles in a magnetic field in a micro-separation column having first and second tubular portions, wherein said first and second tubular portions have different cross-sectional areas, each cross-sectional area having a substantially constant diameter; and eluting the biological material by dissociating the biological material from the superparamagnetic carriers while still in said magnetic field.

14. The process of claim 13, wherein said superparamagnetic carriers comprise superparamagnetic beads.

* * * * *